United States Patent
Seddon

(10) Patent No.: US 6,942,641 B2
(45) Date of Patent: Sep. 13, 2005

(54) CATHETER

(76) Inventor: J. Michael Seddon, 700 Tilghman Dr., Suite 722, Dunn, NC (US) 28334

(*) Notice: Subject to any disclaimer, the term of this patent is extended or adjusted under 35 U.S.C. 154(b) by 102 days.

(21) Appl. No.: 10/449,256

(22) Filed: May 30, 2003

(65) Prior Publication Data
US 2004/0243104 A1 Dec. 2, 2004

(51) Int. Cl.$^7$ ............................................. A61M 29/00
(52) U.S. Cl. ....................................................... 604/107
(58) Field of Search ................................ 604/104–109, 604/96.01, 908, 912, 915

(56) References Cited

U.S. PATENT DOCUMENTS

| | | | |
|---|---|---|---|
| 3,108,595 A | | 10/1963 | Overment |
| 3,397,699 A | * | 8/1968 | Kohl ........................... 604/105 |
| 3,490,457 A | | 1/1970 | Petersen |
| 4,222,384 A | | 9/1980 | Birtwell |
| 4,627,838 A | | 12/1986 | Cross et al. |
| 4,995,868 A | | 2/1991 | Brazier |
| 5,232,440 A | * | 8/1993 | Wilk ............................ 604/543 |
| 5,344,439 A | * | 9/1994 | Otten ........................... 607/126 |
| 5,645,528 A | | 7/1997 | Thome |
| 6,283,940 B1 | * | 9/2001 | Mulholland ............... 604/96.01 |
| 6,527,737 B2 | * | 3/2003 | Kaneshige .................... 604/48 |
| 6,558,350 B1 | | 5/2003 | Hart et al. |
| 2001/0056273 A1 | | 12/2001 | Ewers |

* cited by examiner

*Primary Examiner*—Larry I. Schwartz
*Assistant Examiner*—Michael G. Bogart
(74) *Attorney, Agent, or Firm*—Coats & Bennett, P.L.L.C.

(57) ABSTRACT

The catheter includes an outer tube with an inlet end portion and a stop formed on the inlet end portion. The stop, which normally assumes a collapsed orientation, is moveable between a collapsed orientation and a deployed orientation. The catheter may include at least one of a diagnostic port disposed on the outer tube proximate the bottom of the stop, a locking device proximate the bottom of the catheter for securing the stop in the deployed orientation, and an actuator for operatively moving the stop between collapsed and deployed orientations. Applying force to the actuator moves the stop from the collapsed orientation to the deployed orientation. The actuator may also include a fail-safe mechanism designed to fail when a predetermined amount of force is applied to the actuator.

32 Claims, 7 Drawing Sheets

CATHETER

BACKGROUND OF THE INVENTION

The present invention relates generally to a method and apparatus for draining fluid from a body cavity, and more particularly to a catheter and a method for using the catheter to drain urine from the bladder.

Catheters have been used for centuries to drain fluid from a body cavity, e.g., to drain urine from the bladder. Modern catheters typically include a long narrow tube with a retention device and drainage port disposed at one end and an exit port at the other end. After a medical practitioner inserts the retention end of a catheter into the bladder, the retention device is deployed to hold the catheter in place while urine drains from the drainage port to the exit port.

Conventional retention devices include Malecot wings and balloons, such as those used in the Foley catheter. Catheters with balloon retention devices are inserted into the bladder in a deflated state until the balloon retention device passes through the bladder neck and into the bladder. Once the balloon retention device passes through the bladder neck and resides within the bladder, the medical practitioner inflates the balloon with a fluid. The inflated balloon retains the upper portion of the catheter, including the drainage port in the bladder. Because the balloon essentially blocks the opening in the bladder, the drainage port for draining fluids is typically located above the retention balloon. To release the catheter, the medical practitioner deflates the balloon by withdrawing the fluid from the balloon.

Catheters with Malecot wings normally assume a deployed orientation. Therefore, before catheters with Malecot wings are inserted into the bladder, the Malecot wings must be collapsed. This is accomplished by inserting an external device, i.e., a trocar, to apply pressure to the Malecot wings and force them into a collapsed orientation. After the wings pass through the bladder neck and into the bladder, releasing the pressure, e.g., by removing the trocar, deploys the wings. The deployed wings hold the catheter in place while the urine drains from the bladder. To release the Malecot catheter, the medical practitioner reapplies pressure to the wings by reinserting the trocar to collapse the Malecot wings while the catheter is withdrawn.

Catheters utilizing the above described retention devices have encountered numerous problems over the years. For example, the catheter must include an inflation channel and/or external means for deploying the retention device, which complicates the catheter design and the catheter administration procedure. In addition, when the drainage port is disposed above the retention device, the medical practitioner may begin deploying the retention device while the retention device is still at least partially in the urethra, which may be uncomfortable for the patient. Further, because there is no way for the medical practitioner to know that the retention device is fully collapsed, the medical practitioner may begin removing the catheter from the bladder before the retention device is fully collapsed, which may also cause discomfort to the patient.

SUMMARY OF THE INVENTION

The catheter of the present invention includes an outer tube with an inlet end portion and a stop formed on the inlet end portion. The stop, which normally assumes a collapsed orientation, is moveable between a collapsed orientation and a deployed orientation.

The catheter may include a diagnostic port disposed on the outer tube proximate a bottom of the stop. When the collapsed stop is positioned within an internal cavity, fluid enters the inlet end portion via the diagnostic port and drains from the catheter. The catheter may also include an actuator. Applying force to the actuator moves the stop from the collapsed orientation to the deployed orientation. The actuator may be configured to fail when a predetermined amount of force is applied to the actuator. Further, the actuator may be operatively connected to a locking device operative to lock the stop in a deployed orientation.

The catheter of the present invention is administered by inserting the inlet end portion into the internal cavity until the stop is disposed within the inner cavity, deploying the stop by pulling the actuator, and locking the stop in the deployed orientation by locking the actuator in the locking device.

DETAILED DESCRIPTION OF THE INVENTION

Figure 1:
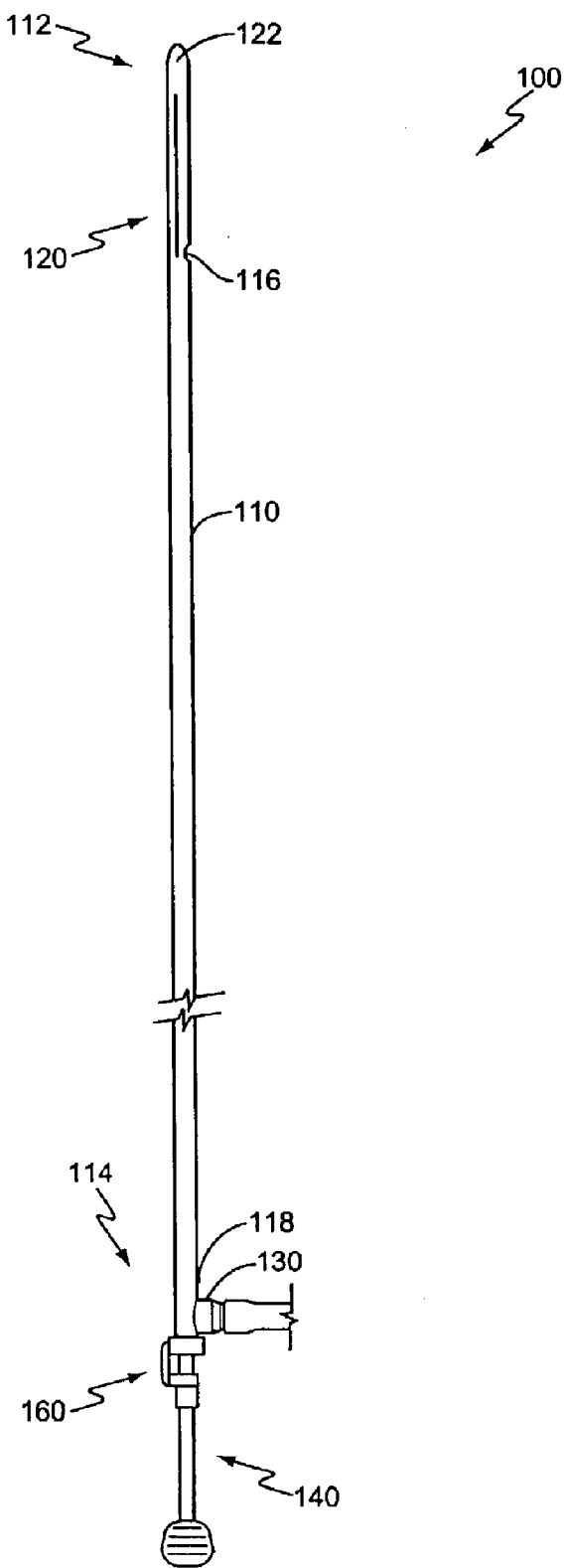
FIG. 1 illustrates a catheter according to the present invention.

FIG. 1 illustrates a catheter 100 according to the present invention. Catheter 100 includes outer sheath 110, inlet end portion 112, and outlet end portion 114. Outer sheath 110 may be constructed from various pliable and resilient materials known in the art, such as rubber, plastic, etc. Inlet end portion 112 includes a stop or retention device 120, tip 122, and diagnostic port 116 disposed proximate the bottom of retention device 120. As used herein, tip 122 of inlet end portion 112 is defined as the area of the inlet end portion 112 between the extreme end of the inlet end portion 112 and the beginning of the retention device 120. As shown in FIG. 1, retention device 120 normally assumes a collapsed orientation.

Outlet end portion 114 includes outlet port 130, actuator 140 extending from outer sheath 110, locking device 160, and diagnostic marker 118. Outlet port 130 provides a drainage outlet for any fluid entering catheter 100 at inlet end portion 112. Actuator 140 connects to inlet end portion 112 as described below and extends through locking device 160 to operatively move retention device 120 from the normal collapsed orientation to a deployed orientation. Actuator 140 also operates to lock retention device 120 in the deployed orientation.

Diagnostic marker 118 aligns with diagnostic port 116, enabling a medical practitioner to position the diagnostic port 116 in a desired location by aligning the diagnostic marker 118. While retention device 120 is in a collapsed orientation, the diagnostic port 116 positioned in the desired location operates as a catheter inlet port on the inlet end portion 112 of catheter 100. As shown in FIG. 1, diagnostic port 116 is disposed proximate the base of retention device 120. As a result, fluid cannot enter diagnostic port 116 and drain from outlet port 130 until the diagnostic port 116, and therefore the entire retention device 120, resides within the internal cavity, i.e., a bladder. A medical practitioner can therefore determine that the retention device 120 resides within the internal cavity once fluid begins exiting outlet port 130. This feature of catheter 100 helps prevent premature deployment of retention device 120.

FIGS. 2A–2C and 3A–3B illustrate exemplary inlet end portions 112 according to the present invention. Inlet end portion 112 includes retention device 120, tip 122, and at least two slits 124 that separate retention device 120 into two sections or wings 126. It will be appreciated by those skilled in the art that inlet end portion 112 may include multiple slits 124 that separate retention device 120 into multiple wings 126.

Figure 2A:
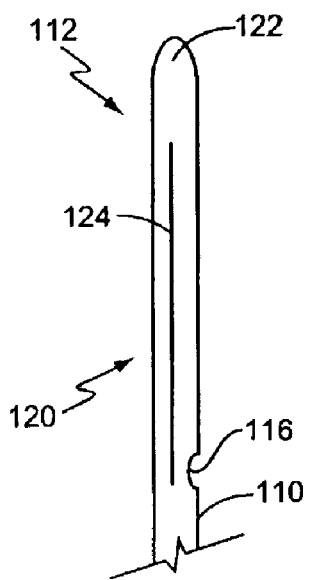
FIGS. 2A, 2B, & 2C illustrate an exemplary inlet end portion of the catheter of FIG. 1.
Figure 2B:
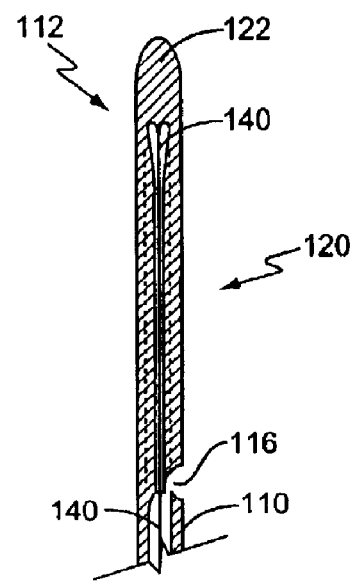
Figure 2C:
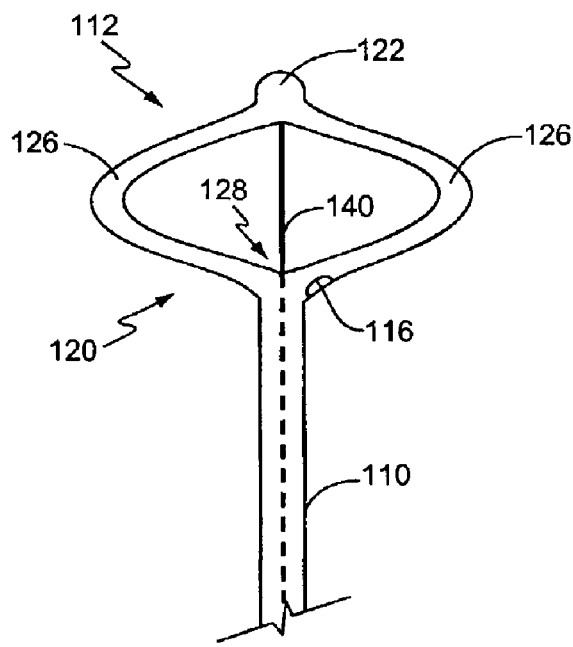

In the embodiment illustrated in FIGS. 2A–2C, actuator 140 includes an elongated strip connected to the tip 122 of inlet end portion 112 (FIG. 2B). When no tension is applied to actuator 140, retention device 120 assumes a collapsed orientation (FIG. 2A). Pulling actuator 140 pulls on tip 122, causing the wings 126 to separate and expand outwardly in a direction generally perpendicular to actuator 140 (FIG. 2C). The separated wings provide access to a drainage opening 128 in outer sheath 110 that serves as a drainage port in the inlet end portion 112. In addition, the expanded wings 126 serve as the retention device 120 to hold the inlet end portion 112 of catheter 100 within the internal cavity. When tension is removed from actuator 140, wings 126 return to a generally collapsed orientation (FIG. 2A).

In the embodiment illustrated in FIGS. 2A–2C, diagnostic port 116 is disposed at the base of one wing 126. As discussed above, diagnostic port 116 provides a catheter inlet port when retention device 120 is disposed in a collapsed orientation. However, diagnostic port 116 becomes ineffective once the retention device 120 has been deployed. After retention device 120 has been deployed, drainage opening 128 provides the primary catheter inlet for draining fluids from the internal cavity.

The embodiment described above and illustrated in FIGS. 2A–2C generally applies to larger catheters 100, because these larger catheters 100 have larger diameter outer sheaths 110 able to accommodate the diameter of the elongated strip actuator 140. However, the elongated strip typically blocks the drainage opening 128 in smaller catheters 100. Therefore, smaller catheters 100 require an alternate actuator 140 to effectively actuate the retention device 120 and drain fluids from the internal cavity.

Figure 3A:
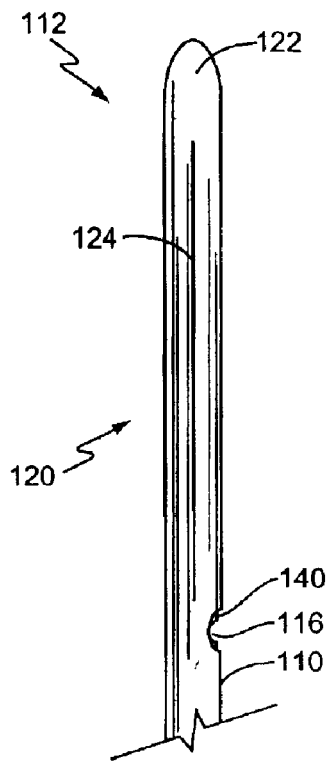
FIGS. 3A & 3B illustrate an alternate inlet end portion of the catheter of FIG. 1.
Figure 3B:
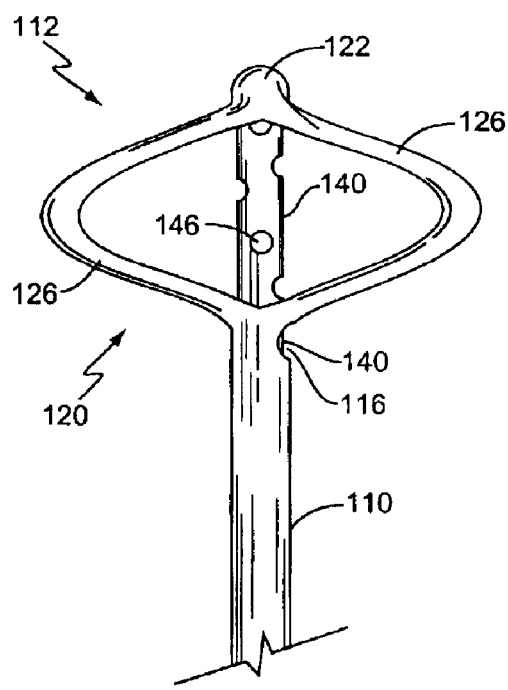

FIGS. 3A–3B illustrate an alternate inlet end portion 112 appropriate for smaller catheters 100. As shown in FIG. 3B, actuator 140 includes an elongated tube connected to the tip 122 of inlet end portion 112 (FIG. 3B). When no tension is applied to actuator 140, retention device 120 assumes a collapsed state (FIG. 3A). Pulling actuator 140 pulls on tip 122, causing the wings 126 to separate and expand outwardly in a direction generally perpendicular to actuator 140 (FIG. 3B). The separated wings provide access to a plurality of drainage holes 146 disposed on a portion of the elongated tube proximate inlet end portion 112 that serve as drainage ports in the inlet end portion 112. Drainage holes 146 provide the necessary catheter inlets while the retention device 120 is in both the collapsed and deployed orientations. As with the previous embodiment, expanded wings 126 serve as the retention device 120 to hold the inlet end portion 112 of catheter 100 within the internal cavity. When tension is removed from actuator 140, wings 126 return to a generally collapsed orientation (FIG. 3A).

In the embodiment of FIGS. 3A–3B, diagnostic port 116 is disposed below retention device 120. When retention device 120 assumes the collapsed state, at least one drainage hole 146 aligns with diagnostic port 116 (FIG. 3A) and provides an inlet for draining fluids and for determining the general location of the retention device 120 relative to the internal cavity, as described above. Once retention device 120 has been deployed, the drainage holes 146 in actuator 140 provide multiple catheter inlets for draining fluids while the elongated tube of actuator 140 blocks diagnostic port 116.

Figure 4A:
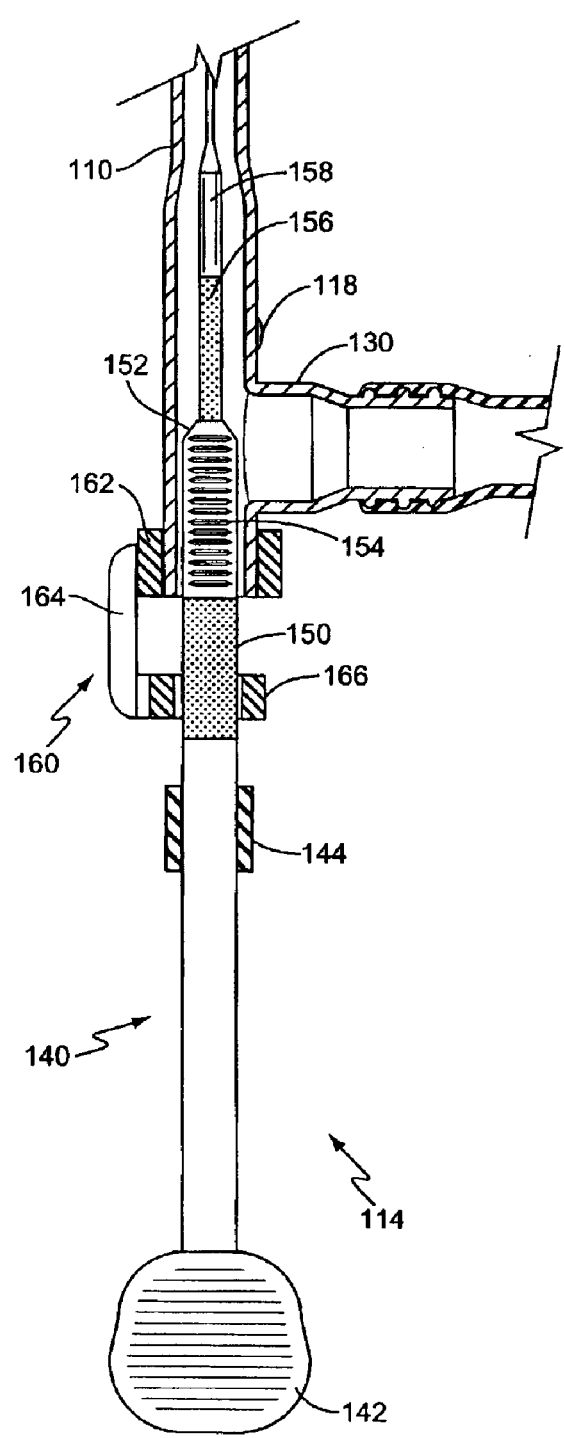
FIG. 4A illustrates an exemplary outlet end portion corresponding to the inlet end portion of Figure FIGS. 2A–2C.
Figure 4B:
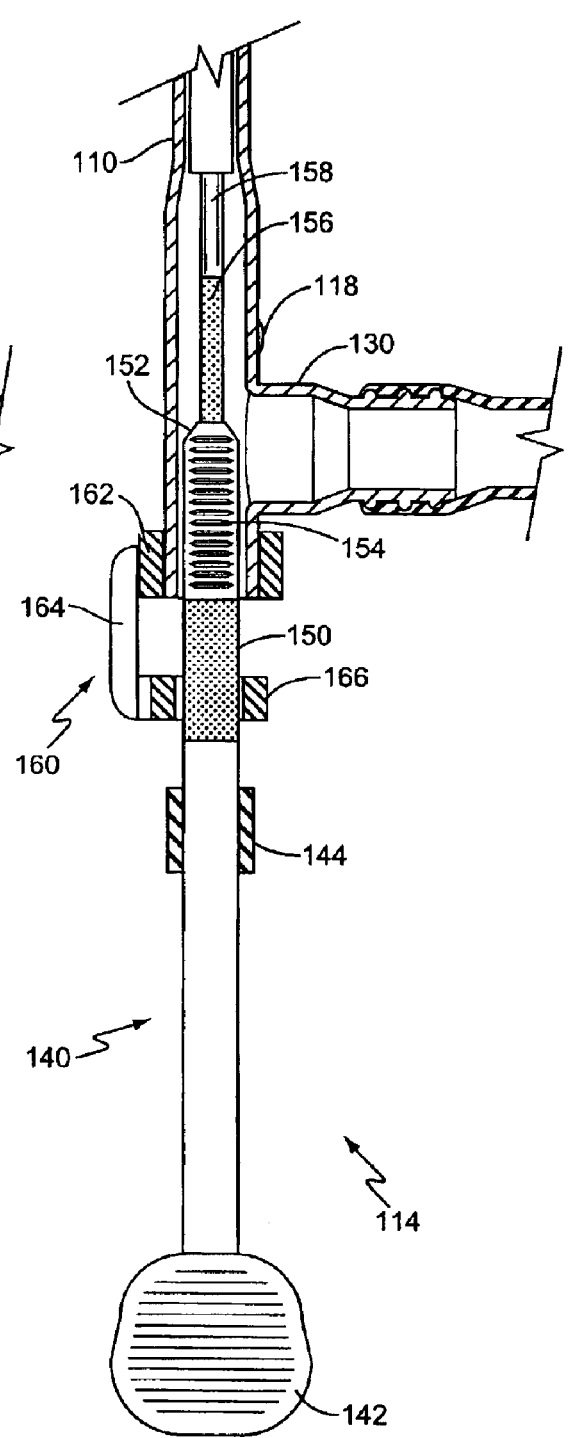
FIG. 4B illustrates an exemplary outlet end portion corresponding to the inlet end portion of Figure FIGS. 3A–3B.

Fluids entering catheter 100 at the inlet end portion 112 will exit at the outlet end portion 114. FIGS. 4A and 4B illustrate exemplary outlet end portions 114 according to the present invention. As described above, outlet end portion 114 comprises outlet port 130, actuator 140, and locking device 160. It will be appreciated that the inlet end portion 112 with the actuator 140 including the elongated strip generally corresponds to the outlet end portion 114 of FIG. 4A, while the inlet end portion 112 with the actuator 140 including the elongated tube generally corresponds to the outlet end portion 114 of FIG. 4B.

Locking device 160 comprises a gripper 162, spacer 164, and lock 166, which includes at least one locking stop. Gripper 162 is secured to outer sheath 110 proximate the outlet end portion 114 with an adhesive or any other suitable securing means known in the art. Lock 166 is connected to and spaced from gripper 162 by spacer 164, includes at least one stop, and operates as a unidirectional lock. The function of locking 166 is discussed further below in conjunction with actuator 140.

Actuator 140 connects to the tip 122 of inlet end portion 112, as discussed above, extends through outer sheath 110, and extends through locking device 160 after exiting outer sheath 110. Actuator 140 may also include an optional handle 142 disposed on an extreme end of actuator 140 to provide a gripping surface for a medical practitioner. Further, actuator 140 may optionally include a stopper 144 that serves as an indicator of the orientation of retention device 120. For example, when retention device 120 is in a collapsed orientation, stopper 144 may be disposed adjacent or proximate locking device 160 (see FIG. 5A). Therefore, stopper 144 indicates to a medical practitioner when the retention device 120 is in a collapsed orientation. As tension is applied to actuator 140, stopper 144 moves away from locking device 160 (see FIGS. 5B–5D), indicating that retention device 120 is no longer in the collapsed orientation. Stopper 144 is typically secured to actuator 140 by an adhesive or any other suitable securing means known in the art.

It is generally useful for a catheter 100 to provide means for deploying the retention device 120, indicating the approximate orientation of the retention device 120, and securing the retention device 120 in the deployed orientation. In the present invention, the actuator 140 may fulfill all three functions. As shown in FIG. 4A actuator 140 includes three or more segments intermediately disposed along actuator 140. These segments generally comprise a deploy segment 150, a locking segment 152, including a plurality of detents 154, and a release segment 156. Each segment may be color-coded according to any convenient color scheme. For example, deploy segment 150 may be yellow, locking segment may be red, and release segment may be blue.

As a medical practitioner pulls actuator 140, retention device 120 begins deploying while deploy segment 150 exits outer sheath 110 and begins passing through locking device 160. Because deploy segment 150 does not lock within lock 166, deploy segment serves several useful functions. For example, deploy segment 150 provides a visible indication to the medical practitioner that the retention device 120 is being deployed. Further, if a patient feels any discomfort while the retention device 120 is being deployed, the medical practitioner may release the actuator 140 to return retention device 120 to a collapsed orientation. As a result, the medical practitioner can reposition inlet end portion 112 before re-deploying retention device 120 without the cumbersome procedures associated with previous devices.

Additional tension on actuator 140 moves deploy segment 150 past locking device 160 and enables locking segment 152 to begin passing through lock 166. As locking segment 152 passes through lock 166, at least one detent 154 locks against a stop disposed in lock 166. As a result, pulling locking segment 152 through lock 166 secures actuator 140 within locking device 160 and operatively locks retention device 120 in a deployed orientation. As mentioned above, lock 166 operates as a unidirectional lock. As used herein, "unidirectional" means that locking segment 152 may be pulled from top to bottom through lock 166, as viewed in FIGS. 5B–5D, but cannot move in the reverse direction.

When the medical practitioner is ready to release retention device 120, actuator 140 is pulled further until release segment 156 is disposed in locking device 160. While release segment 156 is disposed in locking device 160, the medical practitioner breaks the release segment 156 using any severing means well known in the art, such as scissors, a knife, etc. Breaking release segment 156 releases the tension holding retention device 120 in the deployed orientation, and therefore allows retention device 120 to return to the normal collapsed orientation.

As shown in FIGS. 4A and 4B, actuator 140 may optionally include tensile or breakable segment 158 disposed intermediately along actuator 140. Tensile segment 158 is designed to break when a predetermined amount of force is applied to actuator 140. Breaking tensile segment 158 also serves to release the tension on retention device 120, allowing the retention device 120 to return to the normal collapsed orientation. Tensile segment 158 serves as a "fail-safe" mechanism that releases the retention device 120 to prevent the catheter 100 from being unintentionally extracted while the retention device 120 is still deployed.

To further demonstrate the operation of catheter 100, FIGS. 5A–5E illustrate the catheter's various stages of operation. The catheter 100 illustrated in FIGS. 5A–5E has an inlet end portion 112 corresponding to the inlet end portion 112 of FIGS. 2A–2C. However, those skilled in the art will appreciate that the following discussion applies equally well to the inlet end portion 112 of FIGS. 3A–3B.

Figure 5E:
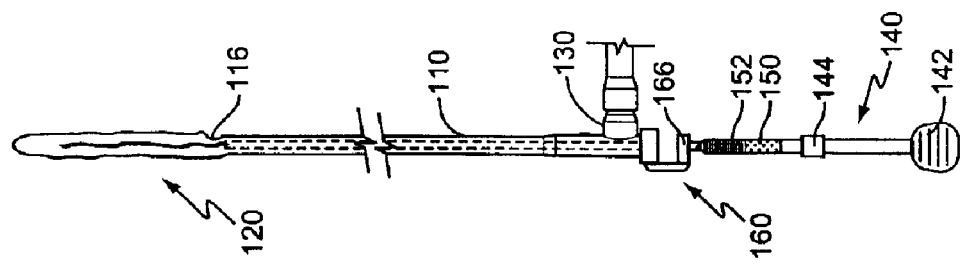
FIG. 5E illustrates the catheter in the collapsed orientation after the actuator has been released.
Figure 5D:
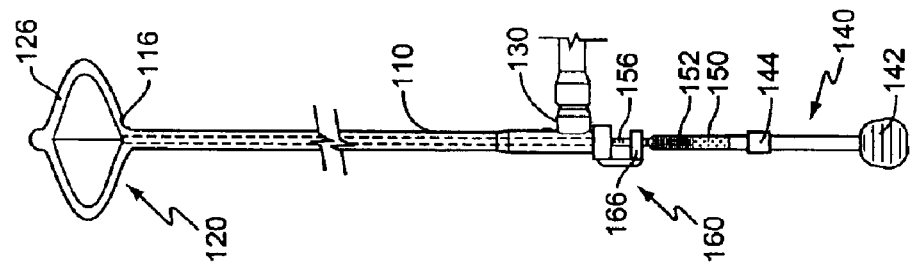
FIG. 5D illustrates the catheter in a pre-release orientation.
Figure 5C:
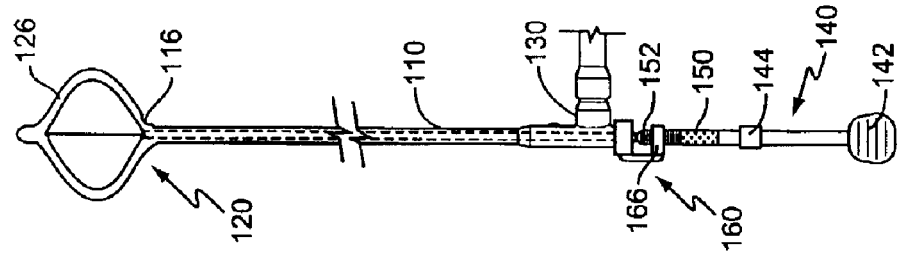
FIG. 5C illustrates the catheter in a fully deployed orientation.
Figure 5B:
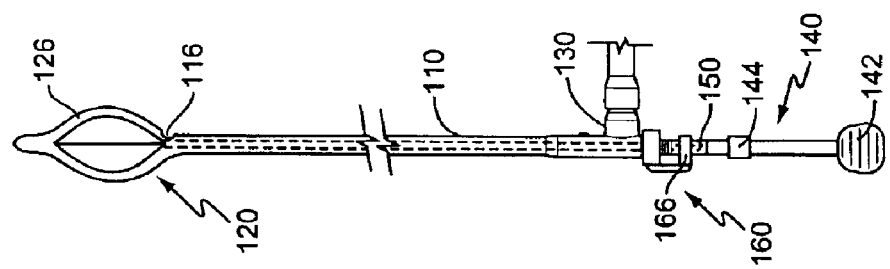
FIG. 5B illustrates the catheter in a partially deployed orientation.
Figure 5A:
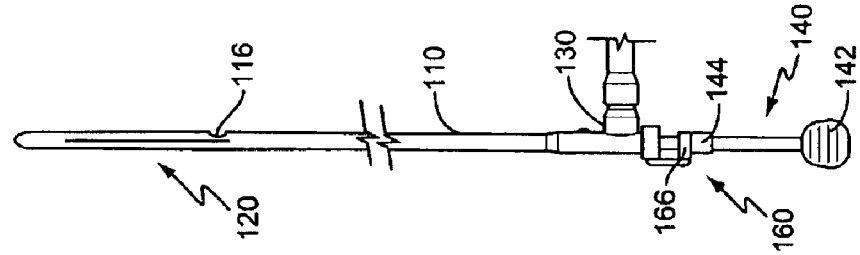
FIG. 5A illustrates the catheter in a collapsed orientation.

FIG. 5A shows catheter 100 in a fully collapsed orientation. As tension is applied to actuator 140, deploy segment 150 begins passing through locking device 160 (FIG. 5B). As shown in FIG. 5B, the tension on actuator 140 causes retention device 120 to begin deploying by causing the wings 126 to separate and expand in a direction perpendicular to actuator 140, as discussed above.

FIG. 5C illustrates catheter 100 with a fully deployed retention device 120. Deploy segment 150 has passed through locking device 160, allowing locking segment 152 to begin passing through lock 166. As described above, as locking segment 152 passes through lock 166, at least one detent 154 on locking segment 152 operatively locks against a stop in lock 166. Locking the actuator 140 in lock 166 operates to lock retention device 120 in the deployed orientation.

By applying additional tension to actuator 140, locking segment 152 passes through lock 166, allowing release segment 156 to begin passing through locking device 160. As shown in FIG. 5D, this causes further expansion of wings 126. Once release segment 156 is disposed within locking device 160, the tension holding retention device 120 in the deployed orientation is released by cutting release segment 156, as described above. Releasing the tension on retention device 120 causes wings 126 to collapse and retention device 120 to generally resume the collapsed orientation (FIG. 5E).

Figure 6B:
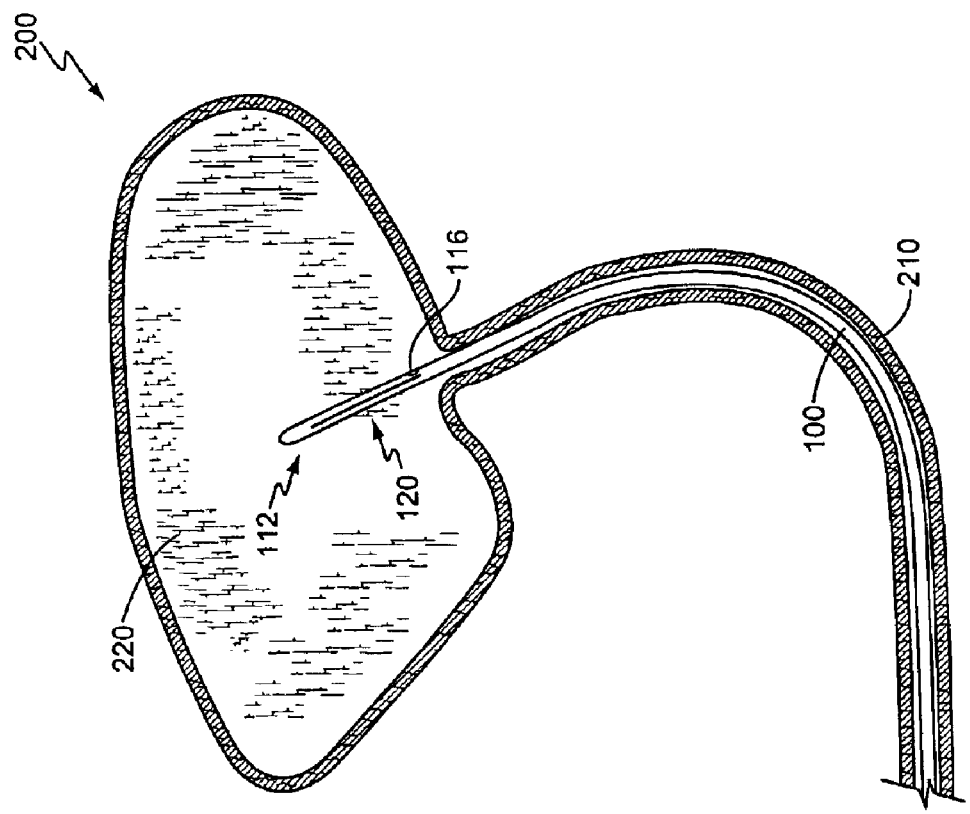
FIG. 6B illustrates inserting the inlet end portion of the catheter into the bladder.
Figure 6A:
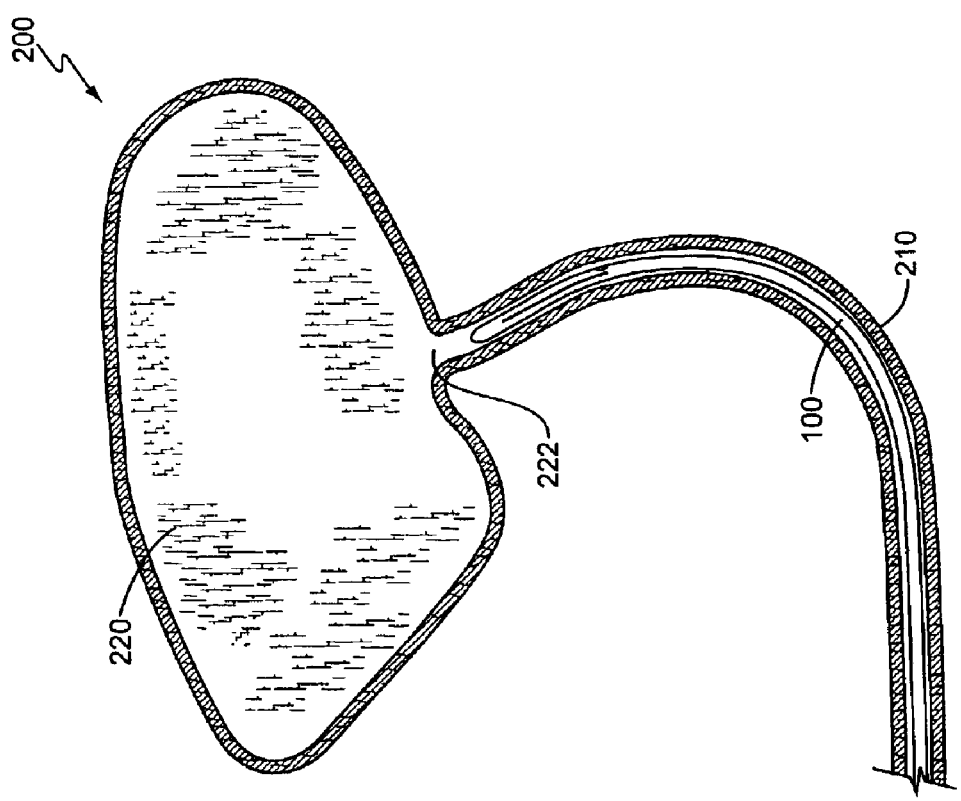
FIG. 6A illustrates the catheter passing through the urinary tract.
Figure 6D:
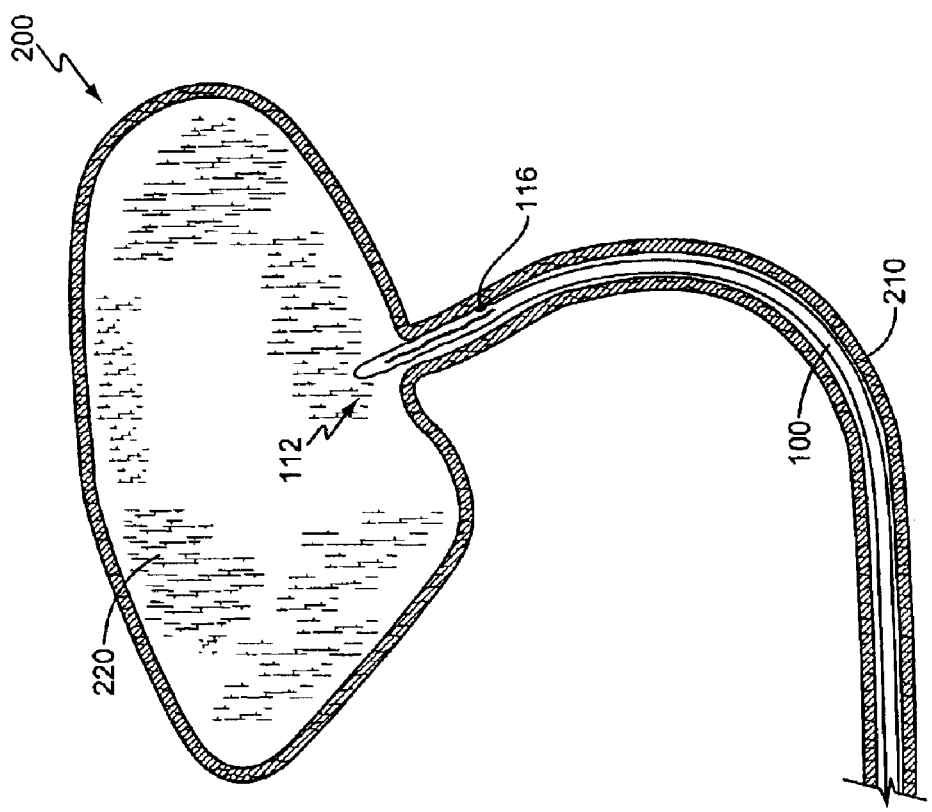
FIG. 6D illustrates removing the released catheter from the urinary tract.
Figure 6C:
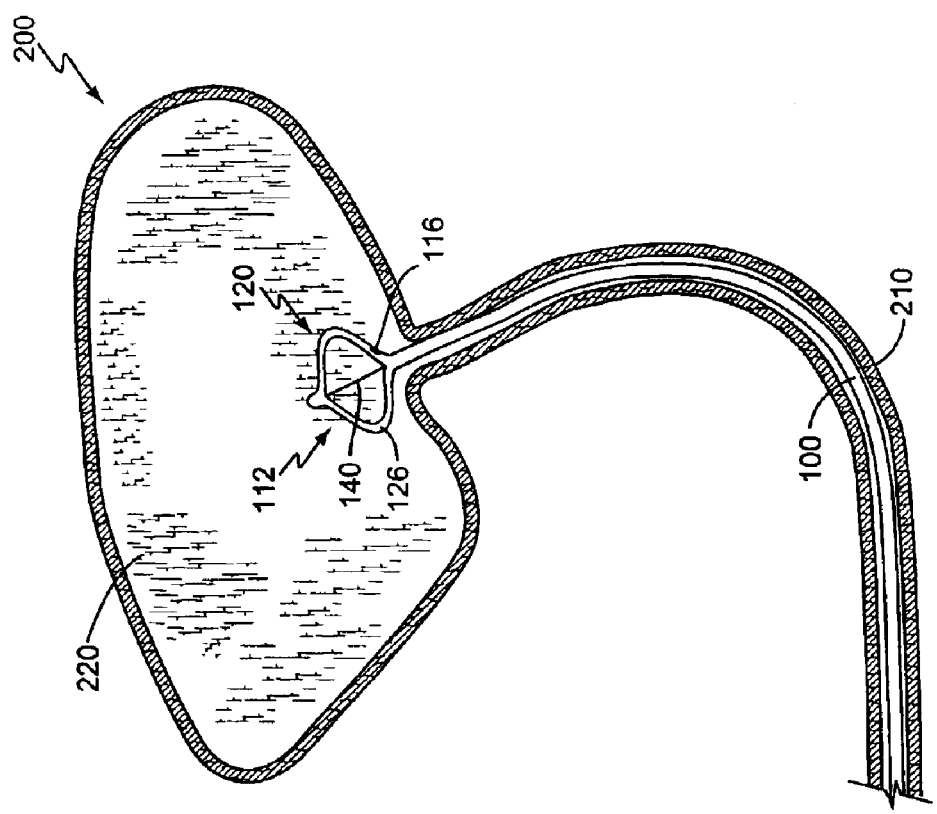
FIG. 6C illustrates a deployed inlet end portion of the catheter in the bladder.

FIGS. 6A–6D illustrate the administration of a catheter into a bladder 220. A medical practitioner inserts the catheter into the urethra 210 of the urinary tract 200 while retention device 120 is in a collapsed orientation (FIG. 6A). Once the entire retention device 120 is disposed within the bladder 220 (FIG. 6B), fluid enters diagnostic port 116 and drains from catheter 100, indicating to the medical practitioner that the retention device 120 is ready to be deployed. Tension is then applied to actuator 140 to deploy retention device 120 and retain inlet end portion 112 in the bladder 220 (FIG. 6C). To remove the catheter 100, tension on retention device 120 is removed by any of the means discussed above to return the retention device 120 to a generally collapsed orientation. The medical practitioner then removes catheter 100 from the bladder 220 (FIG. 6D). While the foregoing describes the administration of catheter 100 into the bladder 220, those skilled in the art will understand that the catheter 100 described above may be used to drain fluids from any internal cavity.

The foregoing description and drawings describe and illustrate the present invention in detail. However, the foregoing only describes some embodiments of a catheter. Accordingly, the present invention may be carried out in specific ways other than those set forth herein without departing from the essential characteristics of the invention. The present embodiments are, therefore, to be considered in all respects as illustrative and not restrictive, and all changes coming within the meaning and equivalency range of the appended claims are intended to be embraced therein.

What is claimed is:

1. A catheter for draining fluid from an internal cavity, the catheter comprising:
    an outer tube including an inlet end portion;
    a stop formed on the inlet end portion and movable between collapsed and deployed orientations;
    a diagnostic port disposed on said outer tube proximate a bottom of said stop for permitting fluid from the internal cavity to enter said outer tube via said diagnostic port when said stop is disposed in the collapsed orientation to verify that said stop is positioned within the internal cavity before said stop is deployed; and
    a diagnostic marker disposed on an exit end portion of said outer tube, opposite said inlet end portion, and aligned with said diagnostic port.

2. The catheter of claim 1 wherein said diagnostic port is disposed on said stop.

3. The catheter of claim 2 wherein said diagnostic port assumes a generally open position when said stop is disposed in either of the collapsed or deployed orientations.

4. The catheter of claim 1 wherein said diagnostic port is disposed below said stop.

5. The catheter of claim 4 wherein said diagnostic port assumes a generally open position when said stop is in the collapsed orientation.

6. The catheter of claim 4 wherein said diagnostic port assumes a generally closed position when said stop is in the deployed orientation.

7. A catheter for draining fluid from an internal cavity, the catheter comprising:
    an outer tube including an inlet end portion;
    a stop formed on the inlet end portion and movable between collapsed and deployed orientations;
    an actuator to operatively move said stop between the collapsed and deployed orientations, wherein said actuator is configured such that said actuator fails in response to a predetermined amount of force being applied to said actuator; and
    a lock for locking said stop in said deployed orientation by locking said actuator in said lock.

8. The catheter of claim 7 wherein said actuator comprises a pull-type actuator including an elongated member, and wherein said elongated member includes a tensile segment that is operative to break in response to said predetermined amount of force being applied to said actuator.

9. The catheter of claim 8 wherein said tensile segment comprises a non-stretchable material.

10. The catheter of claim 8 wherein a first end of said pull-type actuator connects to a tip of said inlet end portion and extends from an exit end portion of said outer tube.

11. The catheter of claim 10 wherein said elongated member further comprises a locking segment proximate said exit end portion of said outer tube and wherein said tensile segment is disposed between said locking segment and said inlet end portion.

12. The catheter of claim 7 wherein when said actuator fails, said actuator moves said stop from the deployed orientation to the collapsed orientation in response to said predetermined amount of force.

13. The catheter of claim 7 wherein said actuator extends through said lock.

14. The catheter of claim 7 wherein said lock operates to unidirectionally lock said actuator.

15. A catheter for draining fluid from an internal cavity, the catheter comprising:
    an outer tube including an inlet end portion;
    a stop formed on the inlet end portion and movable between collapsed and deployed orientations;
    an actuator to operatively move said stop between the collapsed and deployed orientations; and
    a locking device disposed proximate an exit end portion of said outer tube and operatively connected to said actuator for locking said stop in a deployed orientation, wherein said actuator further comprises a release segment disposed between said locking device and said inlet end part on.

16. The catheter of claim 15 wherein said actuator comprises a pull-type actuator including an elongated member, and wherein said elongated member includes a locking segment, said locking segment operatively connected to said locking device.

17. The catheter of claim 16 wherein said locking segment includes one or more detents that lock against one or more stops in said locking device.

18. The catheter of claim 16 said stop assumes a deployed orientation when said locking segment is disposed in said locking device.

19. The catheter of claim 16 wherein said stop assumes a collapsed orientation when no force is applied to said actuator.

20. The catheter of claim 19 wherein the release segment is disposed between said locking segment and said inlet end portion, and wherein said stop assumes a collapsed orientation when said release segment is severed to separate said locking segment from said stop.

21. The catheter of claim 16 wherein said locking segment is disposed proximate an end of said elongated member.

22. A catheter for draining fluid from an internal cavity, the catheter comprising:
    an outer tube including an inlet end portion, wherein said inlet end portion comprises a tip disposed on an extreme end of the inlet end portion;
    a stop formed on the inlet end portion below the tip and movable between normal collapsed and deployed orientations;

an actuator to operatively move said stop between the collapsed and deployed orientations, wherein a first end of said actuator connects to the tip of said inlet end portion; and wherein said stop normally assumes a collapsed orientation but is moveable to a deployed orientation upon actuation of said actuator.

23. The catheter of claim 22 in said outer tube includes two or more slits disposed on said inlet end portion.

24. The catheter of claim 23 wherein said two or more slits disposed on said inlet end portion separate said outer tube into two or more sections.

25. The catheter of claim 24 wherein two or more sections assume the general shape of wings when said stop assumes a generally deployed orientation.

26. The catheter of claim 22 wherein said stop assumes a generally collapsed orientation when a portion of said actuator separates from said inlet end portion.

27. A method of administering a catheter comprising:

inserting an inlet end portion of an outer tube into an internal cavity of a patient until a stop formed on the inlet end portion is disposed within the internal cavity, said stop movable between collapsed and deployed orientations;

deploying said stop in the internal cavity by pulling an actuator attached to a tip of said inlet end portion and extending through a locking device;

locking said stop in the deployed orientation by locking said actuator in said locking device; and determining that said stop is disposed in the internal cavity by draining fluid disposed in the internal cavity from a diagnostic port positioned proximate a bottom of said stop to an exit port disposed proximate said exit end portion.

28. The method of claim 27 further comprising positioning said diagnostic port in a desired orientation in the internal cavity by positioning a diagnostic mark proximate said exit end portion of said outer tube in the desired orientation, wherein said diagnostic mark aligns with said diagnostic port.

29. The method of claim 27 wherein said actuator comprises a locking segment disposed below said tip of said inlet end portion, said locking segment including a detent, and wherein locking said actuator in said locking device comprises positioning said detent in said locking device.

30. The method of claim 29 wherein said actuator comprises at least one release segment disposed between said inlet end portion and said locking segment, the method further comprising returning said stop to a collapsed orientation by separating one of said release segments to disconnect said inlet end portion from said locking segment.

31. The method of claim 30 wherein separating one of said release segments comprises:

pulling said actuator until a first release segment is disposed outside of said outer tube; and cutting said first release segment to separate one of said release segments.

32. The method of claim 30 wherein separating one of said release segments comprises applying a predetermined level of force to said actuator until a second release segment breaks.

* * * * *